United States Patent [19]

Rempfler et al.

[11] 4,425,157
[45] Jan. 10, 1984

[54] PYRIDYLOXY-PHENOXY-ALKANETHIOCARBOXYLIC ACID ESTER DERIVATIVES AND THEIR HERBICIDAL USE

[75] Inventors: Hermann Rempfler, Ettingen; Werner Föry, Basel, both of Switzerland

[73] Assignee: Ciba-Geigy Corporation, Ardsley, N.Y.

[21] Appl. No.: 355,089

[22] Filed: Mar. 5, 1982

Related U.S. Application Data

[60] Division of Ser. No. 140,402, Apr. 14, 1980, Pat. No. 4,329,167, which is a continuation-in-part of Ser. No. 80,965, Oct. 1, 1979, abandoned, which is a continuation of Ser. No. 919,119, Jun. 26, 1978, abandoned.

[30] Foreign Application Priority Data

Jun. 29, 1977 [CH] Switzerland .................. 8023/77

[51] Int. Cl.³ .................. C07D 213/64; A01N 43/40
[52] U.S. Cl. .................. 71/94; 546/302; 546/300
[58] Field of Search .................. 546/300, 302; 71/94

[56] References Cited

U.S. PATENT DOCUMENTS 4,003,734  1/1977  Johnston .................. 71/94
4,046,553  9/1977  Takahashi et al. .................. 71/94

FOREIGN PATENT DOCUMENTS 2288089  5/1976  France .
2329632  5/1977  France .
2359129  2/1978  France .

OTHER PUBLICATIONS

Abstract–Japanese Kokai 51-142537 Aug. 12, 1976.

*Primary Examiner*—Alan L. Rotman
*Attorney, Agent, or Firm*—Frederick H. Rabin; Bruce M. Collins

[57] ABSTRACT

Herbicidal and plant growth-regulating action. Pyridyloxy-phenoxyalkanecarboxylic acid derivatives of the formula

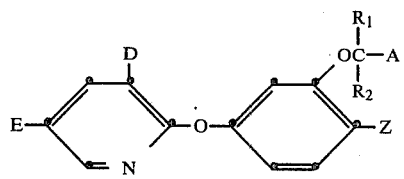

wherein
A is cyano or carboxyl, an ester, thioester or amido radical or the salt of the carboxylic acid with a cation or a quaternary ammonium group,
Z is hydrogen, halogen, cyano, nitro, $C_1$–$C_4$ alkyl or $C_1$–$C_4$ alkoxy,
D is hydrogen, halogen, cyano, nitro or $C_1$–$C_4$ alkoxy,
E is halogen, trifluoromethyl or cyano.
$R_1$ is hydrogen, $C_1$–$C_4$ alkyl, $C_2$–$C_8$ alkoxyalkyl or $C_1$–$C_5$ alkoxy carbonyl and
$R_2$ is hydrogen or $C_1$–$C_4$ alkyl.

21 Claims, No Drawings

PYRIDYLOXY-PHENOXY-ALKANETHIOCARBOXYLIC ACID ESTER DERIVATIVES AND THEIR HERBICIDAL USE

CROSS-REFERENCE TO RELATED APPLICATION

This is a divisional of application Ser. No. 140,402 filed on Apr. 14, 1980, now Pat. No. 4,329,167, which is a continuation-in-part of application Ser. No. 080,965, filed on Oct. 1, 1979, now abandoned. Application Ser. No. 080,965 was a continuation of application Ser. No. 919,119, filed on June 26, 1978, now abandoned.

DETAILED DISCLOSURE

Pyridyloxy-Phenoxyalkanecarboxylic Acid Derivatives

The present invention relates to novel pyridyloxy-phenoxyalkanecarboxylic acid derivatives which have a herbicidal and plant growth-regulating action, processes for their production, compositions which contain these compounds as active ingredients, and to a method of selectively controlling weeds and of regulating plant growth which comprises the use of the novel active substances or of compositions which contain them.

The active compounds of the present invention have the formula I

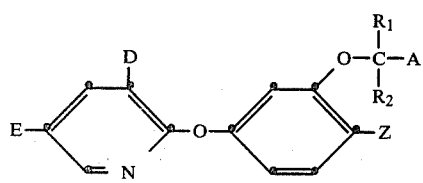

wherein

A represents the cyano group, a radical -COB or a 2-oxazoline radical which is unsubstituted or mono- or polysubstituted by methyl, B represents a radical $-OR_3$, $-SR_3$, $-NR_4R_5$ or $-O-N=C\,(C_1-C_4\,alkyl)_2$ Z and D each individually represent hydrogen, halogen, cyano, nitro, $C_1-C_4$ alkyl or $C_1-C_4$ alkoxy, E represents halogen, trifluoromethyl, cyano or nitro, $R_1$ represents hydrogen, $C_1-C_4$ alkyl or $C_2-C_8$ alkoxyalkyl, or $C_1-C_5$ alkoxycarbonyl $R_2$ represents hydrogen or $C_1-C_4$ alkyl, $R_3$ represents hydrogen, ammonium or an alkali or alkaline earth metal cation, a benzyl or $C_1-C_4$ alkylammonio group, whose alkyl radicals may be substituted by hydroxyl $C_1-C_4$ alkoxy or a $C_1-C_{18}$ alkyl radical which is unsubstituted or substituted by halogen, cyano, $C_1-C_8$ alkoxyalkoxy, $C_2-C_8$ alkoxycarbonyl, bis($C_1-C_4$ alkyl)amino, $C_3-C_8$ cycloalkyl, $C_3-C_8$ cycloalkenyl and also by a 5 to 6-membered heterocyclic radical which is unsubstituted or is itself mono- or polysubstituted by $C_1-C_4$ alkyl;

a $C_3-C_{10}$ alkenyl radical which is unsubstituted or mono- to tetra-substituted by halogen;

a $C_3-C_8$ alkynyl, $C_3-C_8$ cycloalkyl- or $C_3-C_8$ cycloalkenyl radical;

a phenyl or benzyl radical, which is mono- or polysubstituted by halogen, $C_1-C_4$ alkyl, $C_1-C_4$ alkoxy, $C_1-C_4$ alkylthio, nitro, trifluoromethyl, cyano, carboxyl, sulfonyl, hydroxyl, amino or bis($C_1-C_4$ alkyl)amino;

a 5 to 6-membered heterocyclic radical;

$R_4$ represents hydrogen, a $C_1-C_8$ alkyl radical, unsubstituted or substituted by halogen, hydroxyl, cyano, $C_1-C_4$ alkoxy or $C_1-C_4$ alkoxycarbonyl;

$C_3-C_8$ alkenyl, unsubstituted or halogensubstituted;

$C_3-C_8$ alkynyl, $C_3-C_8$ cycloalkyl or $C_3-C_8$ cycloalkenyl;

phenyl or benzyl, unsubstituted or substituted by halogen, $C_1-C_4$ alkyl, $C_1-C_4$ alkoxy, trifluoromethyl, nitro or cyano;

$R_5$ represents the same as $R_4$ or $C_1-C_4$ alkoxy or $C_2-C_4$ alkenyloxy or $R_4$ and $R_5$ together with the nitrogen atom, to which they are attached, form also a 5 to 6-membered heterocyclic ring, which may be substituted by $C_1-C_4$ alkyl.

In the above formula the alkyl radicals can be branched or unbranched and contain the indicated number of carbon atoms. The heterocyclic radicals $R_3$ include, furyl-, tetrahydrofuryl-, oxane-, thiophene-radicals and further, the same that are also found by the symbols $R_4$ and $R_5$ with the nitrogen to which they are attached, pyrrolidine, pyridine, piperidine, morpholine, oxazoline or piperazine. These rings may be substituted by $C_1-C_4$ alkyl radicals.

The active compounds of the formula (I) of the present invention possess a herbicidal action, especially in post-emergent application, and can be used as weed-killers in crops of mono- and dicotyledonous plants. They also possess advantageous growth-regulating effects (growth inhibition). In particular, they inhibit the growth of dicotyledonous plants. Exemplary of the useful application of the compounds of the present invention are:

the reduction of the vegetative growth in soya and similar leguminosae, resulting in an increase in the yield of these plants;

the inhibition of the undesirable growth of suckers in tobacco plants, the leading shoots of which have been cut, thus promoting the formation of larger and finer leaves;

the inhibition of the growth of grass and dicotyledonous plants, such as fruit trees, ornamental trees, bushes and hedgerows, with the object of saving cutting work.

The compounds of the present invention have a low toxicity to warm-blooded animals and their application causes no problems. The rate of application is between 0.1 and 5 kg per hectare.

Good herbicidal activity has been observed with the groups of compounds listed below. They are therefore of special interest among the compounds of formula I.

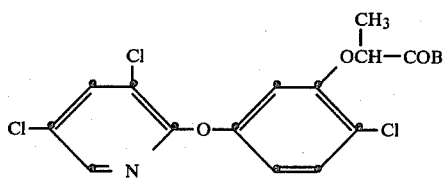

-continued

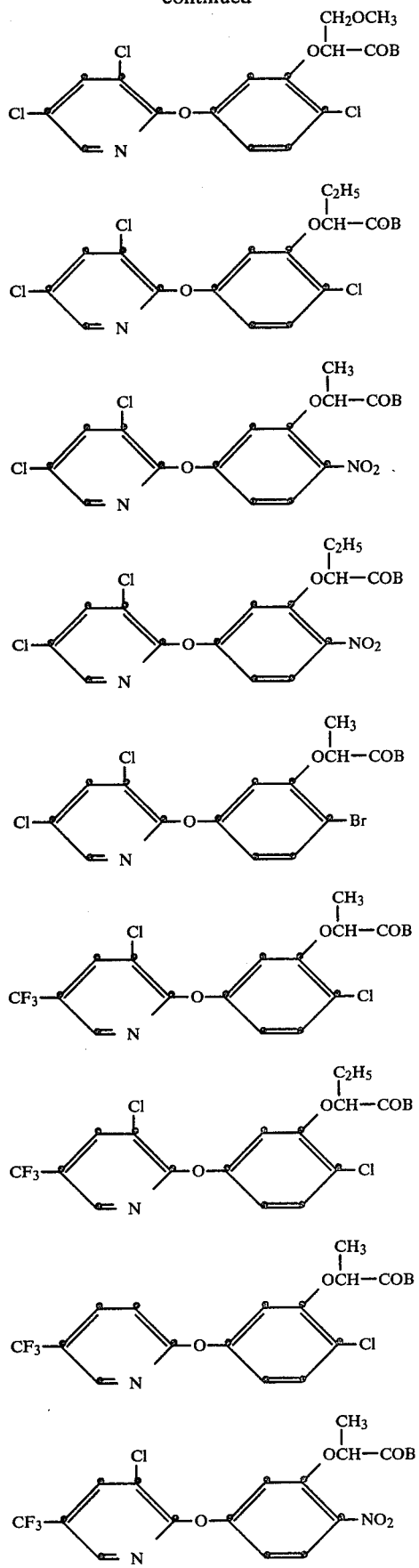

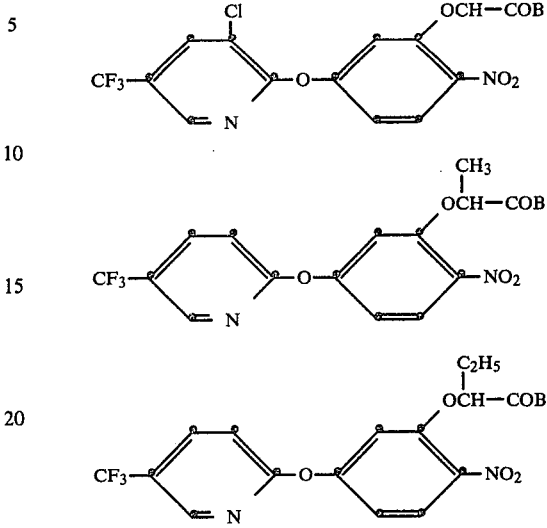

In these formulae, B has the meanings given above under formula I.

From the U.S. Pat. Nos. 4,046,553 and 4,105,435 have become know 4-pyridyloxy-phenoxyalkanecarboxylic acid derivatives with herbicidal activity. The compounds of this invention proved to act differently and are capable of controlling plants, which were not or not satisfactorily controlled with compounds known from these patents.

The novel compounds of the formula (I) can be obtained by processes which are in themselves known. In a first process, a substituted or unsubstituted halopyridine of the formula II,

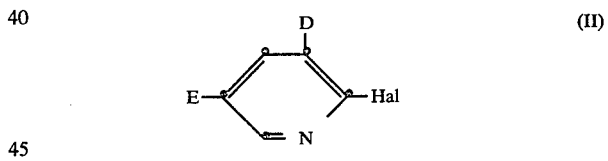

wherein D and E are as defined in formula (I) and Hal represents a halogen atom, preferably a chlorine or bromine atom, is reacted with a hydroxyphenoxyalkanecarboxylic acid derivative of the formula III,

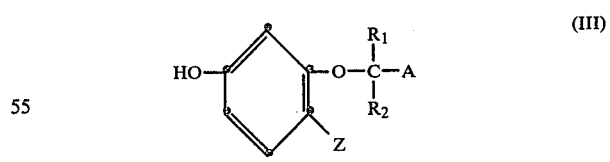

wherein A, C, $R_1$ and $R_2$ are as defined in formula (I), in the presence of an acid acceptor.

Such reactions are in themselves known and the exact method by which they are carried out is described in the literature, for example in Houben-Weyl, Volume 3, page 85 ff.

In a second process, the pyridyloxy-phenoxyalkanecarboxylic acid derivatives of the formula (I) are prepared by reacting a pyridyloxy-hydroxyphenyl ether of the formula IV,

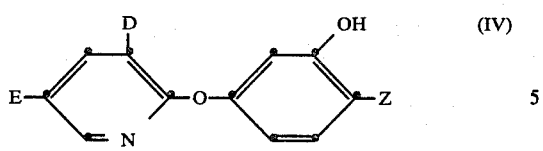

wherein Z, D and E are as defined in formula (I), with an α-halogenocarboxylic acid derivative of the formula V

wherein A, R$_1$ and R$_2$ are as defined in formula (I) and Hal represents a halogen atom, preferably a chlorine or bromine atom, in the presence of an acid acceptor.

The above reactions can be carried out in the presence or absence of solvents or diluents which are intert to the reactants. Polar organic solvents, such as methyl ethyl ketone, acetonitrile, dimethyl formamide, dimethyl sulphoxide etc., are preferred. The reaction temperatures are between 0° and 200° C. and the reaction time is from ¼ hour to several days, depending on the chosen reaction temperature and solvent. The reaction is ordinarily carried out under normal pressure or slight excess pressure. Suitable acid acceptors for the reaction are inorganic bases, for example NaOH, KOH, NaOCH$_3$, NaH, K$_2$CO$_3$, potassium tert-butylate etc., and also organic bases.

A number of the starting materials of the formulae (II) to (V) are known. Starting materials of these formulae which have not yet been described can be easily prepared by conventional processes and techniques.

Substituted 2-halogeno-pyridines of the formula (II) can be easily obtained from the corresponding 2-pyridinoles, some of which are known. Starting materials of the formula (III) can be obtained by reacting, for example, a monobenzyl ether of an optionally substituted resorcinol with an α-halogenocarboxylic acid derivative, preferably an ester of the formula (V), and cleaving the benzyl-phenyl ether bond by catalytic hydrogenation, for example with a palladium on carbon catalyst, whereby the benzyl radical is removed as toluene.

The starting materials of the formula (IV) can be obtained by reaction of resorcinol with halopyridines in equimolar amounts and in the presence of a base.

Carboxylic acid derivatives of the formula (V) are also known. As their simplest representatives, mention may be made for example of chloroacetic acid and the esters, thioesters and amides thereof. However, other α-halocarboxylic acid derivatives substituted in accordance with R$_1$ and R$_2$ are also suitable.

The following Examples illustrate the process of the present invention for obtaining arbitrarily chosen active compounds of the formula (I). Further active compounds which are obtained in corresponding manner are listed in the subsequent tables.

These pyridyloxy-phenoxyalkanecarboxylic acid derivatives of the formula (I) are stable compounds which are soluble in conventional organic solvents, such as alcohols, ethers, ketones, dimethyl formamide, dimethyl sulphoxide etc.

EXAMPLE 1

α-[3-(3',5'-Dichloropyrid-2-yl)-oxy-phenoxy]propionic acid methyl ester (intermediate)

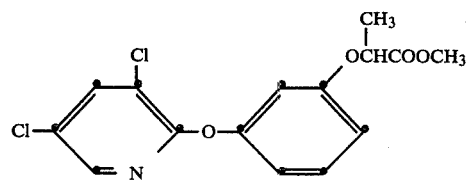

30.8 g (0.1 mole) of 3-(3',5'-dichloropyrid-2'-yl)-oxy-phenoxy phenol, 18.2 g (0.13 mole) of potassium carbonate and 22 g of methyl α-bromopropionate are refluxed in 300 ml of ethyl ketone for 3 hours. The inorganic salts are then filtered off and the filtrate is concentrated. Recrystallization of the residue from ether/petroleum ether affords 29 g (70% of theory) of the title product with a melting point of 58°–60° C.

EXAMPLE 2

α-[3-(3',5'-Dichloropyridyl-2'-oxy)-6-nitrophenoxy]-propionic acid methyl ester

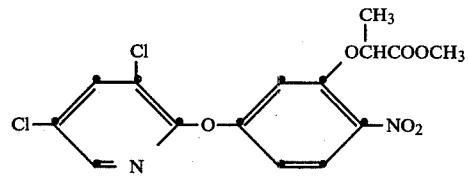

(a) 171 g (0.5 mole) of α-[3-(3',5'-dichloropyrid-2-yl)oxy-phenoxy]propionic acid (prepared according to Example 1) are dissolved in 250 ml of 1,2 dichloroethane. The reaction is then cooled to −12° to −14° C. and during 2 hours there is added dropwise 250 ml of 100% nitric acid. After ½ hour, the reaction mixture is poured into ice-water. The mixture is then extracted methylene chloride. The organic phase is washed twice with water, dried over magnesium sulfate and evaporated. The residue is taken up in 500 ml of hexane and triturated, which causes it to crystallise. The cristals are filtered and dried to yield 172.3 g (89% of theory) of the title compound which melts at 107°–108° C.

This compound can also be produced in the following manner.

(b) 30.1 g (0.1 mole) of 3-(3',5'-dichloropyridyl-2'-oxy)-6-nitrophenol, 16.7 g (0.1 mole) of methyl α-bromopropionate and 20.7 g (0.15 mole) of potassium carbonate are refluxed for 14 hours in 400 ml of methyl ethyl ketone. The inorganic salts are filtered off and the filtrate is concentrated. The residual brown oil is taken up in chloroform and filtered over a short column of silica gel, affording 22.4 g (58% of theory) of title product which melts at 107° C. after recrystallisation from hexane.

EXAMPLE 3

3-(3',5'-Dichloropyridyl-2'-oxy)-6-chlorophenyl acetate (intermediate)

A mixture of 256 g of 3-(3',5'-dichloropyridyl-2'-oxy)-phenol, 1.9 liters of glacial acetic acid and 280 ml of acetic anhydride is stirred for 12 hours at reflux temperature. The solution is cooled to 40° C., then 81 g of sodium acetate are added with stirring and 106 g of chlorine gas are introduced at 40° C. in the course of 7 hours. Excess chlorine gas is removed by introducing nitrogen for 2 hours and the solution is concentrated. The ethyl acetate solution (1000 ml) of the oily residue is washed with water and saturated NaHCO$_3$ solution and concentrated, affording 343 g of the title compound as a brown oil which crystallises spontaneously on trituration with petroleum ether.

Melting point: 71°–75° C.

EXAMPLE 4

3-(3',5'-Dichloropyridyl-2'-oxy)-6- and 4-chlorophenol (intermediate)

A suspension of 2.26 g of powdered KOH and 10 g of 3-(3',5'-dichloropyridyl-2'-oxy)-6-phenyl acetate in 30 ml of absolute methanol is stirred for 20 minutes at 60° C. in a nitrogen atmosphere, cooled to room temperature, acidified with 3.7 ml of concentrated hydrochloric acid and concentrated. The toluene solution (50 ml) of the residue is washed with water, dried, filtered over activated carbon and concentrated, affording 8.4 g of an oil which consists of a mixture of the 6-chlorophenol and 4-chlorophenol isomers in the ratio 7:3.

EXAMPLE 5

α-[3-(3',5'-Dichloropyridyl-2'-oxy)-6-chlorophenoxy]-propionic acid methyl ester

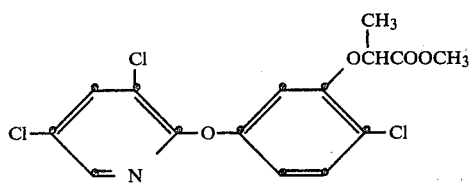

25 g (0.085 mole) of a mixture of 3-(3',5'-dichloropyridyl-2'-oxy)-6-chlorophenol and 3-(3',5'-dichloropyridyl-2'-oxy)-4-chlorophenol (prepared according to Example 4), 14.2 g (0.085 mole) of methyl α-bromopropionate and 13.8 g (0.01 mole) of potassium carbonate are refluxed for 6 hours in 250 ml of methyl ethyl ketone. The inorganic salts are filtered off and the filtrate is concentrated. The residual yellow oil is recrystallised from ether/petroleum ether, affording 30.1 g (94% of theory) if isomer-free title product with a melting point of 82°–83° C.

EXAMPLE 6

3-(3',5'-Dichloropyridyl-2'-oxy)-6-bromophenyl acetate (intermediate)

A mixture of 205 g of 3-(3',5'-dichloropyridyl-2'-oxy)-phenol, 1.1 liters of glacial acetic acid and 224 ml of acetic anhydride is stirred for 12 hours at reflux temperature. The solution is cooled to 60° C., then 64.8 g of sodium acetate are added with stirring and a solution of 102 ml of bromine in 400 ml of glacial acetic acid are added dropwise at 60° C. in the course of 5¾ hours. The solution is concentrated and the residue is dissolved in ethyl acetate. The organic phase is washed in succession with water and saturated NaHCO$_3$ solution. The combined ethyl acetate extracts are dried and concentrated, affording 302.5 g of an oil which crystallises on being covered with a layer of petroleum ether (b.p. 60°–90° C.). After recrystallisation from cyclohexane, the title product melts at 106°–107° C.

EXAMPLE 7

3-(3',5'-Dichloropyridyl-2'-oxy)-6-bromophenol (intermediate)

A suspension of 28 g of powdered KOH and 153.5 g of 3-(3',5'-dichloropyridyl-2'-oxy)-6-bromophenyl acetate in one liter of absolute methanol is stirred for 20 minutes at 60° C. in a nitrogen atmosphere and concentrated. The concentrate is acidified at room temperature with concentrated hydrochloric acid and evaporated to dryness. The toluene solution (400 ml) of the residue is washed with water, dried, and concentrated. The oily residue is triturated with petroleum ether/cyclohexane and filtered, affording 137 g of the crystalline title product with a melting point of 93°–95° C.

EXAMPLE 8

α-[3-(3',5'-Dichloropyridyl-2'-oxy)-6-bromophenoxy]-propionic acid methyl ester

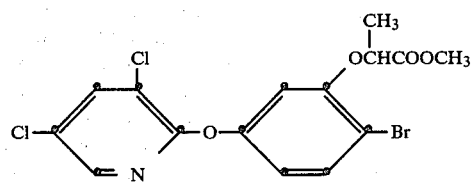

50.2 g (0.15 mole) of 3-(3',5'-dichloropyridyl-2'-oxy)-6-bromophenol (prepared according to Example 7), 27.5 g (0.165 mole) of methyl α-bromopropionated and 27.6 g (0.2 mole) of potassium carbonate are refluxed for 5 hours in 250 ml of methyl ethyl ketone. The inorganic salts are filtered off and the filtrate is concentrated. The residual reddish oil is recrystallised from ether/petroleum ether, affording 58 g (91.8% of theory) of the title compound with a melting point of 75° C.

Analogously to these Examples, the following compound can be prepared:

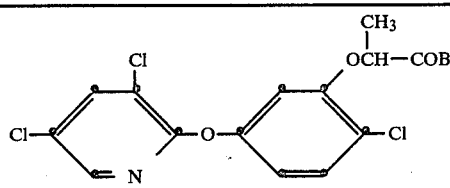

| No. | B | phys. data |
|---|---|---|
| 1 | OCH$_3$ | m.p. 82–83° |
| 2 | OC$_2$H$_5$ | m.p. 53–56° |
| 3 | OC$_3$H$_7$ iso | n$_D^{25}$ 1.5567 |
| 4 | OC$_3$H$_7$n | |
| 5 | OC$_4$H$_9$n | n$_D^{25}$ 1.5540 |
| 6 | OC$_4$H$_9$ sec. | n$_D^{25}$ 1.5525 |
| 7 | OC$_4$H$_9$ tert. | |
| 8 | OC$_4$H$_9$ iso | n$_D^{25}$ 1.5538 |
| 9 | OCH(CH$_3$)C$_3$H$_7$n | |
| 10 | OCH(CH$_3$)C$_5$H$_{11}$n | |
| 11 | OC$_8$H$_{17}$n | |
| 12 | OC$_2$H$_4$OCH$_3$ | n$_D^{25}$ 1.5547 |
| 13 | OC$_2$H$_4$OC$_2$H$_5$ | |
| 14 | OC$_2$H$_4$Cl | n$_D^{25}$ 1.5722 |
| 15 | OC$_2$H$_4$Br | |
| 16 | 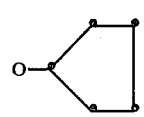 | n$_D^{30}$ 1.5617 |

| | | |
|---|---|---|
| 17 | 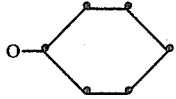 | |
| 18 | 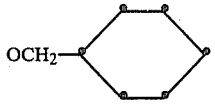 | $n_D^{30}$ 1.5565 |
| 19 | OCH₂CH=CH₂ | $n_D^{25}$ 1.5629 |
| 20 | OC₂H₄—CH=CH₂ | |
| 21 | OCH₂C(CH₃)=CH₂ | |
| 22 | OCH₂C≡CH | m.p. 64–68° |
| 23 | OCH(CH₃)C≡CH | |
| 24 |  | |
| 25 | 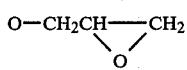 | |
| 26 | OCH₂CN | |
| 27 | OC₂H₄OC₄H₉n | $n_D^{30}$ 1.5445 |
| 28 | SCH₃ | $n_D^{25}$ 1.5850 |
| 29 | SC₂H₅ | |
| 30 | SC₃H₇n | |
| 31 | SC₃H₇ iso | |
| 32 | SC₄H₉ iso | |
| 33 | SCH₂CH=CH₂ | |
| 34 | SCH₂—CH=CH—CH₃ | |
| 35 | SCH₂COOCH₃ | $n_D^{40}$ 1.5788 |
| 36 | 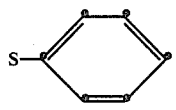 | |
| 37 | O⁻Na⁺ | m.p. 98–101 |
| 38 | O⁻NH₄⁺ | |
| 39 | NH₂ | m.p. 142–5° |
| 40 | N(CH₃)₂ | |
| 41 | NHC₂H₅ | m.p. 112–5° |
| 42 | NHC₂H₄OH | |
| 43 | NH(CH₂)₃OCH₃ | m.p. 90–92° |
| 44 | NHC₂H₄OCH₃ | m.p. 89–91° |
| 45 | NHC₂H₄Cl | |
| 46 | NHCH₂CH=CH₂ | m.p. 119–120° |
| 47 | N(CH₂CH=CH₂)₂ | |
| 48 | NHC₃H₇ iso | |
| 49 | N(C₂H₅)₂ | m.p. 73–4° |
| 50 | NHC₄H₉n | |
| 51 | NHC₅H₁₁ iso | |
| 52 |  | |
| 53 |  | m.p. 39–42° |
| 54 | NHCH₂COOC₂H₅ | |
| 55 | N(CH₃)OCH₃ | m.p. 75–7° |
| 56 | ON=C(CH₃)C₂H₅ | |
| 57 | ON=C(CH₃)₂ | |

| | | |
|---|---|---|
| 58 |  | |
| | 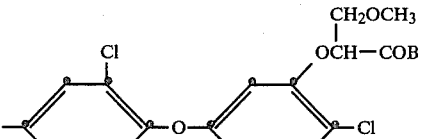 | |
| 59 | OCH₃ | |
| 60 | OC₂H₅ | |
| 61 | OCH₂—CH=CH₂ | |
| 62 | OC₃H₆OCH₃ | |
| 63 | SCH₃ | |
| 64 | SCH₂C≡CH | |
| 65 | NHCH₃ | |
| 66 | N(CH₃)OCH₃ | $n_D^{30}$ 1.5613 |
| | 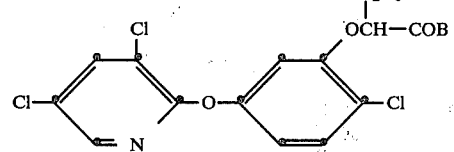 | |
| 67 | OCH₃ | m.p. 88–89° |
| 68 | OC₂H₅ | $n_D^{30}$ 1.5620 |
| 69 | OC₃H₇ iso | $n_D^{30}$ 1.5563 |
| 70 | OC₄H₉ iso | |
| 71 | OC₂H₄OCH₃ | |
| 72 | OCH₂CN | |
| 73 | ON=C(CH₃)₂ | |
| 74 | OCH₂COOCH₃ | |
| 75 | SCH₃ | |
| 76 | SC₃H₇ iso | |
| 77 | SC₅H₁₁n | |
| 78 | NH₂ | |
| 79 | NHC₂H₅ | m.p. 104–5° |
| 80 | N(C₂H₅)₂ | |
| 81 | NHCH₃ | |
| 82 | NHCH₂CH=CH₂ | |
| 83 | NHCH₂C≡CH | |
| 84 | N(CH₃)OCH₃ | $n_D^{25}$ 1.5660 |
| 85 | 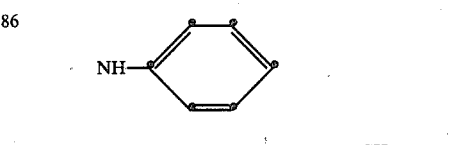 | |
| 86 | 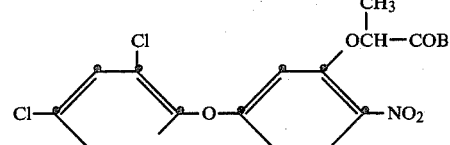 | |
| | 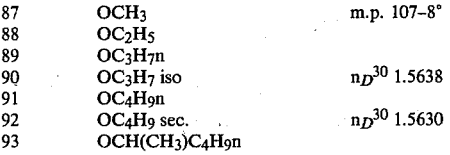 | |
| 87 | OCH₃ | m.p. 107–8° |
| 88 | OC₂H₅ | |
| 89 | OC₃H₇n | |
| 90 | OC₃H₇ iso | $n_D^{30}$ 1.5638 |
| 91 | OC₄H₉n | |
| 92 | OC₄H₉ sec. | $n_D^{30}$ 1.5630 |
| 93 | OCH(CH₃)C₄H₉n | |
| 94 | OC₈H₁₇n | |
| 95 | OC₂H₄OCH₃ | $n_D^{30}$ 1.5709 |

| | | |
|---|---|---|
| 96 | OCH(CH$_3$)COOCH$_3$ | |
| 97 | OC$_2$H$_4$Cl | |
| 98 | OCH$_2$CH=CH$_2$ | n$_D^{30}$ 1.5771 |
| 99 | OCH$_2$C(CH$_3$)=CH$_2$ | |
| 100 | OCH$_2$C≡CH | |
| 101 | 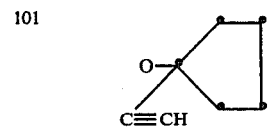 | |
| 102 | OCH(CH$_3$)C≡CH | |
| 103 | OC$_2$H$_4$N(CH$_3$)$_2$ | n$_D^{40}$ 1.5699 |
| 104 | 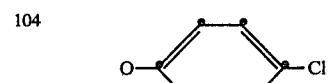 | |
| 105 | 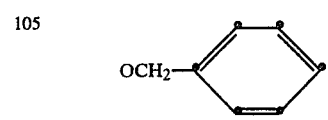 | |
| 106 | SCH$_3$ | |
| 107 | SC$_2$H$_5$ | |
| 108 | SC$_4$H$_9$ iso | |
| 109 | SCH$_2$CH=CH$_2$ | |
| 110 | SCH$_2$C(CH$_3$)=CH$_2$ | n$_D^{30}$ 1.5920 |
| 111 | SCH$_2$C≡CH | m.p. 92–95° |
| 112 | NH$_2$ | m.p. 135–7° |
| 113 | NHCH$_3$ | m.p. 126–7° |
| 114 | N(CH$_3$)$_2$ | m.p. 116–7° |
| 115 | NHC$_2$H$_5$ | m.p. 128–9° |
| 116 | N(C$_2$H$_5$)$_2$ | m.p. 88–9° |
| 117 | NHC$_3$H$_7$n | m.p. 112–4° |
| 118 | NHC$_3$H$_7$ iso | m.p. 112–3° |
| 119 | NHCH$_2$CH=CH$_2$ | m.p. 108–11° |
| 120 | N(CH$_2$CH=CH$_2$)$_2$ | n$_D^{30}$ 1.5760 |
| 121 | NHCH$_2$C≡CH | m.p. 148–150° |
| 122 | NHC$_4$H$_9$n | |
| 123 | NHC$_4$H$_9$ sec. | |
| 124 | NHC$_4$H$_9$ iso | |
| 125 | NHC$_5$H$_{11}$ iso | m.p. 95–98° |
| 126 | NHC$_6$H$_{13}$n | m.p. 87–90° |
| 127 | NHC$_2$H$_4$OCH$_3$ | m.p. 101–3° |
| 128 | NH(CH$_3$)OCH$_3$ | m.p. 93–4° |
| 129 | NHC(CH$_3$)$_2$C≡CH | m.p. 118–120° |
| 130 | NHCH$_2$COOC$_2$H$_5$ | |
| 131 | 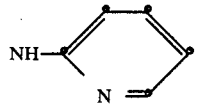 | m.p. 116–8° |
| 132 | 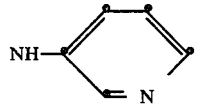 | m.p. 118–120° |
| 133 | 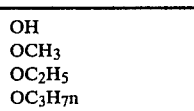 | m.p. 113–116° |
| 134 | 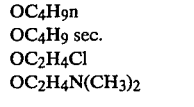 | m.p. 132–134° |
| 135 | 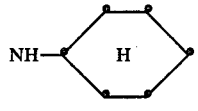 | m.p. 130–132° |
| 136 |  | |
| 137 | 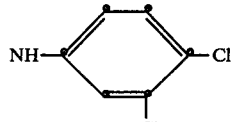 | m.p. 148–151° |
| 138 | 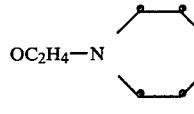 | m.p. 134–137° |
| 139 | 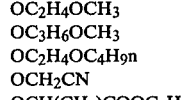 | m.p. 117–119° |
| 140 | NHC$_3$H$_6$OC$_2$H$_5$ | |
| 141 | NHC$_3$H$_6$OCH$_3$ | n$_D^{40}$ 1.5738 |
| 142 | NHC$_2$H$_4$OC$_2$H$_5$ | |
| 143 | NHC$_8$H$_{17}$n | |
| 144 | OH | m.p. 134–6° |
| 145 | O$^⊖$NH$_3$C$_3$H$_7$ iso | |
| 146 | ON=C(CH$_3$)$_2$ | |

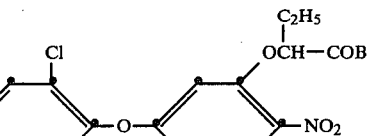

| | | |
|---|---|---|
| 147 | OH | |
| 148 | OCH$_3$ | m.p. 80–2° |
| 149 | OC$_2$H$_5$ | n$_D^{25}$ 1.5511 |
| 150 | OC$_3$H$_7$n | |
| 151 | OC$_3$H$_7$ iso | n$_D^{30}$ 1.5585 |
| 152 | OC$_4$H$_9$n | |
| 153 | OC$_4$H$_9$ sec. | n$_D^{30}$ 1.5590 |
| 154 | OC$_2$H$_4$Cl | |
| 155 | OC$_2$H$_4$N(CH$_3$)$_2$ | n$_D^{30}$ 1.5715 |
| 156 | OC$_2$H$_4$—N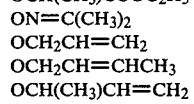 | |
| 157 | OC$_2$H$_4$OCH$_3$ | |
| 158 | OC$_3$H$_6$OCH$_3$ | |
| 159 | OC$_2$H$_4$OC$_4$H$_9$n | |
| 160 | OCH$_2$CN | |
| 161 | OCH(CH$_3$)COOC$_2$H$_5$ | n$_D^{30}$ 1.5525 |
| 162 | ON=C(CH$_3$)$_2$ | n$_D^{30}$ 1.5665 |
| 163 | OCH$_2$CH=CH$_2$ | n$_D^{30}$ 1.5735 |
| 164 | OCH$_2$CH=CHCH$_3$ | |
| 165 | OCH(CH$_3$)CH=CH$_2$ | |
| 166 | OCH$_2$C≡CH | n$_D^{30}$ 1.5795 |
| 167 | OC(CH$_3$)$_2$C≡CH | |

| | | |
|---|---|---|
| 168 | 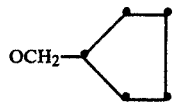 | |
| 169 |  | |
| 170 | 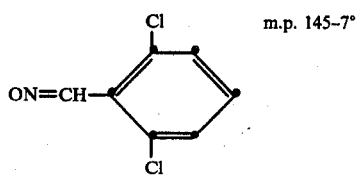 | m.p. 145–7° |
| 171 |  | |
| 172 | SCH$_3$ | n$_D^{30}$ 1.6015 |
| 173 | SC$_2$H$_5$ | n$_D^{30}$ 1.5933 |
| 174 | SC$_4$H$_9$ iso | |
| 175 | SCH$_2$COOCH$_3$ | |
| 176 | NH$_2$ | m.p. 156–9° |
| 177 | NHCH$_3$ | m.p. 132–4° |
| 178 | N(CH$_3$)$_2$ | m.p. 118–120° |
| 179 | NHC$_2$H$_5$ | |
| 180 | N(C$_2$H$_5$)$_2$ | |
| 181 | NHC$_3$H$_7$ iso | |
| 182 |  | |
| 183 | NHCH$_2$COOCH$_3$ | |
| 184 | 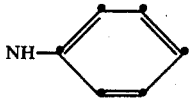 | |
| 185 |  | |
| 186 | NHC$_2$H$_4$OCH$_3$ | m.p. 118–120° |
| 187 | NHC$_3$H$_6$OCH$_3$ | m.p. 90–92° |
| 188 | NHCH$_2$CH=CH$_2$ | m.p. 104–6° |
| 189 | N(CH$_2$CH=CH$_2$)$_2$ | |
| 190 | N(CH$_3$)OCH$_3$ | n$_D^{30}$ 1.5800 |
| 191 | NHOCH$_2$CH=CH$_2$ | |

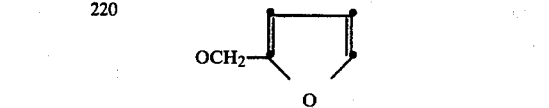

| | | |
|---|---|---|
| 192 | OCH$_3$ | m.p. 75° |
| 193 | OC$_2$H$_5$ | |
| 194 | OC$_3$H$_7$ iso | m.p. 60–3° |
| 195 | OCH(CH$_3$)C$_3$H$_7$n | n$_D^{30}$ 1.5561 |
| 196 | OC$_2$H$_4$OC$_2$H$_5$ | n$_D^{30}$ 1.5631 |
| 197 | OC$_2$H$_4$Cl | n$_D^{30}$ 1.5792 |
| 198 | OC$_8$H$_{17}$n | n$_D^{30}$ 1.5458 |
| 199 | OCH$_2$CH=CHCH$_3$ | n$_D^{30}$ 1.5730 |
| 200 | OCH$_2$C≡CH | m.p. 80–82° |
| 201 | 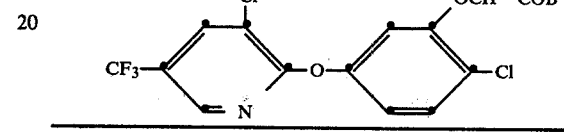 | n$_D^{30}$ 1.5811 |
| 202 | SC$_3$H$_7$ iso | n$_D^{30}$ 1.5795 |
| 203 | SC$_4$H$_9$ iso | n$_D^{30}$ 1.5805 |
| 204 | SCH$_2$COOCH$_3$ | n$_D^{30}$ 1.5780 |
| 205 | SCH(CH$_3$)C$_2$H$_5$ | n$_D^{30}$ 1.5778 |
| 206 | NH$_2$ | m.p. 155–156° |
| 207 | NHC$_2$H$_5$ | m.p. 114–115° |
| 208 | N(CH$_3$)OCH$_3$ | |
| 209 | OH | m.p. 150–1° |

| | | |
|---|---|---|
| 210 | OCH$_3$ | m.p. 74–77° |
| 211 | OC$_2$H$_5$ | |
| 212 | OC$_3$H$_7$n | |
| 213 | OC$_3$H$_7$ iso | |
| 214 | OC$_4$H$_9$ iso | |
| 215 | OC$_6$H$_{13}$n | |
| 216 | OC$_2$H$_4$Cl | |
| 217 | OC$_2$H$_4$N(CH$_3$)$_2$ | |
| 218 | OC$_2$H$_4$OC$_4$H$_9$ | |
| 219 | OCH$_2$CH—CH$_2$ (epoxide) | |
| 220 | OCH$_2$–(furan) | |
| 221 | OCH$_2$–C$_6$H$_4$Cl | |
| 222 | OCH$_2$CH=CH$_2$ | |
| 223 | OCH(CH$_3$)CH=CH$_2$ | |
| 224 | OCH$_2$C≡CH | |
| 225 | OCH(CH$_3$)C≡CH | |
| 226 | SCH$_3$ | |
| 227 | SCH$_2$CH=CH$_2$ | |
| 228 | SCH(CH$_3$)CH=CH$_2$ | |
| 229 | SCH$_2$C≡CH | |
| 230 | S–C$_6$H$_5$ | |
| 231 | SCH$_2$–C$_6$H$_5$ | |
| 232 | OH | |
| 233 | O$^\ominus$H$_3$N$^\oplus$(C$_3$H$_7$ iso)$_2$ | |
| 234 | O$^\ominus$Na$^\oplus$ | |
| 235 | O$^\ominus$NH$_4^\oplus$ | |
| 236 | NH$_2$ | |
| 237 | NHCH$_3$ | |
| 238 | N(C$_2$H$_5$)$_2$ | |

-continued

| | |
|---|---|
| 239 | NHC$_4$H$_9$ iso |
| 240 | NHC$_2$H$_4$OCH$_3$ |
| 241 | NHC$_3$H$_6$OC$_2$H$_5$ |
| 242 | N(CH$_3$)OCH$_3$ |

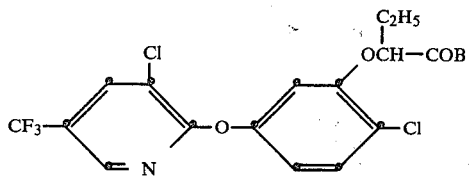

| | | |
|---|---|---|
| 243 | OH | |
| 244 | OCH$_3$ | |
| 245 | OC$_3$H$_7$ iso | |
| 246 | OC$_4$H$_9$ n | |
| 247 | SCH$_3$ | |
| 248 | SCH$_2$—CH=CH$_2$ | |
| 249 | SCH$_2$COOCH$_3$ | |
| 250 | SC$_2$H$_4$OCH$_3$ | |
| 251 | SC$_4$H$_9$ iso | |

252 [structure: SCH$_2$-phenyl-Cl]

253 [structure: SCH$_2$-phenyl-Br]

| | |
|---|---|
| 254 | NH$_2$ |
| 255 | NHC$_2$H$_5$ |
| 256 | N(CH$_3$)$_2$ |
| 257 | NHCH$_2$CH=CH$_2$ |
| 258 | N(CH$_3$)OCH$_3$ |
| 259 | NHC$_5$H$_{11}$n |

[structure: CF$_3$-phenyl-O-phenyl(OCH(CH$_3$)-COB)-Cl]

| | | |
|---|---|---|
| 260 | OH | |
| 261 | OCH$_3$ | $n_D^{25}$ 1.5150 |
| 262 | OC$_2$H$_5$ | |
| 263 | OC$_3$H$_7$n | |
| 264 | OC$_3$H$_7$ iso | |
| 265 | OCH$_2$CH=CH$_2$ | |
| 266 | OCH$_2$C≡CH | |
| 267 | OCH(CH$_3$)COOC$_2$H$_5$ | |
| 268 | NH$_2$ | |
| 269 | NHCH$_3$ | |
| 270 | N(CH$_3$)$_2$ | |
| 271 | N(C$_3$H$_7$ iso)$_2$ | |
| 272 | NHCH$_2$CH=CH$_2$ | |
| 273 | NHCH$_2$CH≡CH | |

[structure: CF$_3$-pyridinyl(Cl)-O-phenyl(OCH(CH$_3$)-COB)-NO$_2$]

| | | |
|---|---|---|
| 274 | OH | |
| 275 | OCH$_3$ | m.p. 74–75° |
| 276 | OC$_2$H$_5$ | |
| 277 | OCH$_2$CN | |
| 278 | OC$_3$H$_7$n | |
| 279 | OC$_3$H$_7$ iso | |
| 280 | OC$_4$H$_9$n | |

-continued

| | |
|---|---|
| 281 | OCH$_2$CH=CH$_2$ |
| 282 | OCH$_2$CH=CHCH$_3$ |
| 283 | OCH$_2$C≡CH |
| 284 | SCH$_3$ |
| 285 | SC$_2$H$_5$ |
| 286 | SC$_3$H$_7$ iso |
| 287 | SCH$_2$CN |
| 288 | SCH$_2$COOCH$_3$ |
| 289 | NH$_2$ |
| 290 | NHCH$_3$ |
| 291 | N(CH$_3$)$_2$ |
| 292 | NH(C$_3$H$_7$ iso) |
| 293 | NHCH$_2$CH=CH$_2$ |

294 [structure: N-containing 6-membered ring]

[structure: CF$_3$-pyridinyl(Cl)-O-phenyl(OCH(C$_2$H$_5$)-COB)-NO$_2$]

| | | |
|---|---|---|
| 295 | OH | |
| 296 | OCH$_3$ | |
| 297 | OC$_2$H$_5$ | $n_D^{30}$ 1.5223 |
| 298 | OC$_3$H$_7$n | |
| 299 | OC$_4$H$_9$ iso | |
| 300 | OCH$_2$CH=CH$_2$ | |
| 301 | OCH$_2$C≡CH | |
| 302 | OCH(CH$_3$)C≡CH | |
| 303 | OC$_4$H$_9$n | |
| 304 | OC$_4$H$_9$ tert. | |
| 305 | OC$_4$H$_9$ sec. | |
| 306 | OC$_2$H$_4$OCH$_3$ | |
| 307 | OC$_2$H$_4$OC$_4$H$_9$n | |
| 308 | OC$_2$H$_4$Cl | |
| 309 | OC$_2$H$_4$Br | |
| 310 | OCH$_2$CH=CHCH$_2$Cl | |
| 311 | OCH$_2$C(CH$_3$)=CH$_2$ | |
| 312 | OC$_2$H$_4$N(CH$_3$)$_2$ | |
| 313 | OC$_2$H$_4$N(C$_2$H$_5$)$_2$ | |
| 314 | OCH(CH$_3$)COOC$_2$H$_5$ | |
| 315 | OCH(C$_2$H$_5$)$_2$ | |
| 316 | SH | |
| 317 | SCH$_3$ | |
| 318 | SC$_2$H$_5$ | |
| 319 | SCH$_2$COOC$_2$H$_5$ | |
| 320 | SCH$_2$CH=CH$_2$ | |
| 321 | SCH$_2$C≡CH | |
| 322 | SC$_4$H$_9$n | |
| 323 | SCH$_2$—CH(CH$_3$)=CH$_2$ | |
| 324 | SCH(CH$_3$)C≡CH | |
| 325 | NH$_2$ | m.p. 127–128° |
| 326 | NHC$_2$H$_4$OCH$_3$ | |
| 327 | NHC$_3$H$_6$OCH$_3$ | |
| 328 | N(C$_2$H$_4$OH)$_2$ | |
| 329 | NHC$_2$H$_4$COOCH$_3$ | |
| 330 | NHCH$_2$COOCH$_3$ | |
| 331 | NHC$_2$H$_4$OH | |
| 332 | NHCH$_3$ | m.p. 113–114° |
| 333 | N(CH$_3$)$_2$ | |
| 334 | NHC$_2$H$_5$ | |
| 335 | N(C$_2$H$_5$)$_2$ | |
| 336 | NHC$_3$H$_7$n | |
| 337 | NHC$_4$H$_9$n | |

338 [structure: N-S containing 6-membered ring]

| | |
|---|---|
| 339 | N(CH$_3$)OCH$_3$ |

-continued

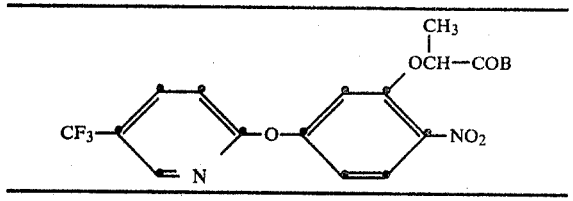

| No. | | | | |
|---|---|---|---|---|
| 340 | OH | | | |
| 341 | OCH$_3$ | | m.p. 89–93° | |
| 342 | OC$_2$H$_5$ | | $n_D^{20}$ 1.5340 | |
| 343 | OCH$_2$CH=CH$_2$ | | | |
| 344 | SCH$_2$CH=CH$_2$ | | | |
| 345 | SCH$_3$ | | | |
| 346 | SCH$_2$COOCH$_3$ | | | |
| 347 | NH$_2$ | | | |
| 348 | NHCH$_3$ | | | |
| 349 | N(CH$_3$)$_2$ | | | |
| 350 | NHC$_2$H$_5$ | | | |
| 351 | NHCH$_2$CH=CH$_2$ | | | |

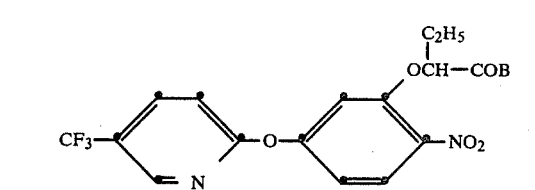

| No. | | | |
|---|---|---|---|
| 352 | OH | | |
| 353 | OCH$_3$ | | |
| 354 | OC$_2$H$_5$ | $n_D^{30}$ 1.5167 | |
| 355 | OC$_3$H$_7$ iso | | |
| 356 | OC$_2$H$_4$OCH$_3$ | | |
| 357 | OCH$_2$CH=CH$_2$ | | |
| 358 | OCH$_2$≡CH | | |
| 359 | SCH$_3$ | | |
| 360 | SC$_2$H$_5$ | | |
| 361 | SCH$_2$CH=CH$_2$ | | |
| 362 | NH$_2$ | | |
| 363 | N(CH$_3$)$_2$ | | |
| 364 | NHC$_2$H$_5$ | | |
| 365 | NHC$_2$H$_4$OCH$_3$ | | |
| 366 | N(CH$_3$)OCH$_3$ | | |

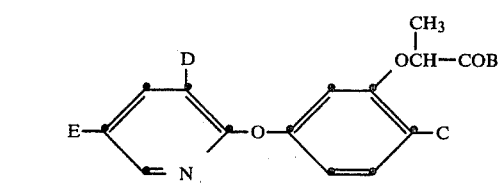

| No. | E | D | Z | B | phys. data |
|---|---|---|---|---|---|
| 367 | Cl | Br | Cl | OCH$_3$ | |
| 368 | Cl | Br | Cl | OC$_2$H$_5$ | |
| 369 | I | H | NO$_2$ | OCH$_3$ | $n_D^{25}$ 1.6125 |
| 370 | I | H | Cl | OCH$_3$ | $n_D^{25}$ 1.5995 |
| 371 | Br | Br | NO$_2$ | OCH$_3$ | m.p. 118–120° |
| 372 | CN | Cl | Cl | OCH$_3$ | m.p. 109–111° |
| 373 | Br | CN | Cl | OCH$_3$ | m.p. 135–7° |
| 374 | Cl | H | Cl | OCH$_3$ | b.p. 145–150°/0.04 |
| 375 | Cl | H | NO$_2$ | NH$_2$ | |
| 376 | Br | H | NO$_2$ | OC$_2$H$_5$ | |
| 377 | Br | H | Cl | OCH$_2$CH=CH$_2$ | |
| 378 | CN | Cl | Br | OCH$_3$ | m.p. 107–9° |
| 379 | CF$_3$ | Cl | Br | OCH$_3$ | |
| 380 | Cl | CH$_3$ | Cl | OCH$_3$ | |
| 381 | Cl | CH$_3$ | Br | OC$_2$H$_5$ | |
| 382 | Cl | CH$_3$ | NO$_2$ | OCH$_3$ | |
| 383 | Cl | CH$_3$ | NO$_2$ | NHCH$_3$ | |
| 384 | CF$_3$ | H | Br | OCH$_3$ | |
| 385 | CF$_3$ | Br | Cl | OCH$_3$ | |
| 386 | Br | Br | Br | OCH$_3$ | m.p. 64–6° |
| 387 | Br | Br | NO$_2$ | OCH$_3$ | m.p. 118–120° |
| 388 | Br | Br | Br | SCH$_3$ | |
| 389 | Br | Br | Cl | OCH$_3$ | m.p. 86–8° |
| 390 | Cl | H | Br | OCH$_3$ | m.p. 80–2° |

-continued

| 391 | CF$_3$ | Br | NO$_2$ | NH$_2$ | |
|---|---|---|---|---|---|
| 392 | CF$_3$ | Br | NO$_2$ | NHCH$_3$ | |

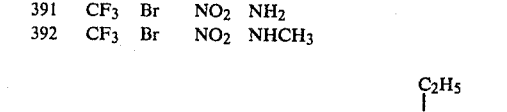

| 393 | Cl | Br | NO$_2$ | OC$_2$H$_5$ | $n_D^{25}$ 1.5820 |
|---|---|---|---|---|---|
| 394 | CN | Cl | NO$_2$ | OC$_2$H$_5$ | |
| 395 | Cl | CH$_3$ | NO$_2$ | OC$_2$H$_5$ | |
| 396 | Cl | CH$_3$ | NO$_2$ | NH$_2$ | |
| 397 | Br | Br | NO$_2$ | OC$_2$H$_5$ | |
| 398 | CF$_3$ | Br | NO$_2$ | OC$_2$H$_5$ | |

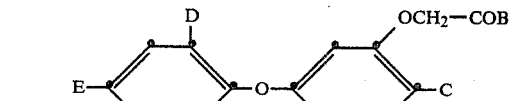

| 399 | Cl | Cl | NO$_2$ | OCH$_3$ | m.p. 83–5° |
|---|---|---|---|---|---|
| 400 | Cl | Cl | NO$_2$ | NH$_2$ | m.p. 203–5° |
| 401 | Cl | Cl | NO$_2$ | NHC$_2$H$_5$ | m.p. 124–5° |
| 402 | Cl | Cl | NO$_2$ | N(CH$_3$)OCH$_3$ | m.p. 106–7° |
| 403 | Cl | Cl | NO$_2$ | OC$_2$H$_4$OCH$_3$ | m.p. 71–2° |
| 404 | Cl | Cl | Br | OCH$_3$ | m.p. 81–2° |
| 405 | Cl | CH$_3$ | NO$_2$ | OCH$_3$ | |
| 406 | CF$_3$ | Cl | NO$_2$ | OCH$_3$ | |
| 407 | CF$_3$ | H | NO$_2$ | OCH$_2$CH=CH$_2$ | |
| 408 | CF$_3$ | H | Cl | OCH$_3$ | |
| 409 | CF$_3$ | Cl | Cl | OCH$_3$ | |

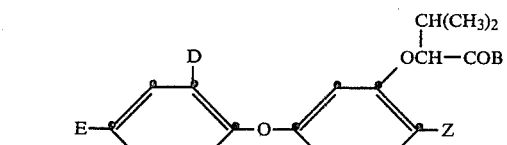

| 410 | Cl | Cl | Cl | OCH$_3$ | $n_D^{30}$ 1.5586 |
|---|---|---|---|---|---|
| 411 | Cl | Cl | NO$_2$ | OCH$_3$ | $n_D^{30}$ 1.5527 |
| 412 | Cl | Cl | NO$_2$ | OC$_2$H$_5$ | |
| 413 | Cl | Cl | NO$_2$ | NHCH$_3$ | |
| 414 | CF$_3$ | H | NO$_2$ | OCH$_3$ | |
| 415 | CF$_3$ | Cl | NO$_2$ | OC$_2$H$_5$ | |
| 416 | CF$_3$ | Cl | Cl | OCH$_3$ | |
| 417 | Br | Br | NO$_2$ | OCH$_3$ | |

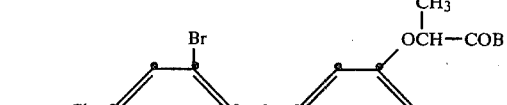

| No. | B | phys. data |
|---|---|---|
| 418 | OCH$_3$ | m.p. 93–94° |
| 419 | OC$_2$H$_5$ | |
| 420 | OC$_2$H$_4$OCH$_3$ | |
| 421 | NH$_2$ | m.p. 145–146° |
| 422 | NHCH$_3$ | m.p. 132–134° |
| 423 | N(CH$_3$)$_2$ | m.p. 136–137° |
| 424 | NHC$_2$H$_5$ | m.p. 124–126° |
| 425 | N(C$_2$H$_5$)$_2$ | m.p. 75–77° |

-continued $$\underset{E}{\overset{D}{\diagdown}}\underset{N}{\diagup}\text{—O—}\diagdown\underset{Z}{\diagup}\text{O—CH—A}\overset{R_1}{|}$$

| No. | E | D | Z | $R_1$ | A | phys. data |
|---|---|---|---|---|---|---|
| 426 | Cl | Cl | $NO_2$ | H | CN | m.p. 118–120° |
| 427 | Cl | Cl | Cl | $CH_3$ | CN | m.p. 119–120° |
| 428 | Cl | Cl | Cl | H | CN | m.p. 101–3° |
| 429 | Cl | Cl | Cl | $CH_3$ | $\begin{array}{c}O\\ \diagup\\ C\\ \diagdown\!\!\diagdown\\ N\end{array}$ | m.p. 133–5° |
| 430 | Cl | Cl | Cl | $CH_3$ | $\begin{array}{c}O\text{—}CH_3\\ \diagup\\ C\\ \diagdown\!\!\diagdown\\ N\end{array}$ | |
| 431 | Cl | Cl | $NO_2$ | $CH_3$ | $\begin{array}{c}O\\ \diagup\\ C\\ \diagdown\!\!\diagdown\\ N\end{array}$ | |

The compositions of the present invention are obtained in known manner by homogeneously mixing and grinding active substances of the general formula I with suitable carriers, with or without the addition of dispersants or solvents which are inert to the active substances. The active substances can be processed to the following formulations:

solid formulations: dusts, tracking powders, granules (coated granules, impregnated granules and homogeneous granules);
active substance concentrates which are dispersible in water: wettable powders, pastes, emulsions;
liquid formulations: solutions.

The concentration of active substance in the above described compositions is between 0.1 and 95%, preferably between 1 and 80%. The rates of application are ordinarily from 0.1 to 10 kg, preferably from 0.25 to 5 kg, of active substance per hectare. The compositions of the present invention can also be mixed with other biocidal active substances or compositions.

The active substances of the formula I can be formulated for example as follows (parts are by weight):

Dusts: The following substances are used to prepare (a) 5% and (b) a 2% dust:
(a)
  5 parts of α-[3-(3',5'-dichloropyridyl-2'-oxy)-6-chlorophenoxy]propionic acid methyl ester,
  95 parts of talc;
(b)
  2 parts of active substance
  1 part of highly dispersed silicic acid
  97 parts of talc.

The active substances are mixed with the carriers and ground.

Granulate: The following substances are used to prepare a 5% granulate:
  5 parts of the above active substance
  0.25 parts of epichlorohydrin
  0.25 parts of cetyl polyglycol ether
  3.25 parts of polyethylene glycol
  91 parts of kaolin (particle size 0.3–0.8 mm).

The active substance is mixed with epichlorohydrin and the mixture is dissolved in 6 parts of acetone. Then polyethylene glycol and cetyl polyglycol ether are added. The resulting solution is sprayed on kaolin and subsequently evaporated in vacuo.

Wettable Powders: The following constituents are used to prepare (a) a 50%, (b) a 25% and (c) a 10% wettable powder:
(a)
  50 parts of α-[3-(3',5'-dichloropyridyl-2'-oxy)-6-bromophenoxy]propionic acid methyl ester
  5 parts of sodium dibutylnaphthylsulphonate
  3 parts of naphthalenesulfonic acid/phenolsulphonic acid/formaldehyde condensate (3:2:1)
  20 parts of kaolin
  22 parts of Champagne chalk;
(b)
  25 parts of the above active substance
  5 parts of sodium oleylmethyltauride
  2.5 parts of naphthalenesulphonic acid/formaldehyde condensate
  0.5 parts of carboxymethyl cellulose
  5 parts of neutral potassium aluminium silicate
  62 parts of kaolin;
(c)
  10 parts of the above active substance
  3 parts of a mixture of the sodium salts of saturated fatty alcohol sulphates
  5 parts of naphthalenesulphonic acid/formaldehyde condensate
  82 parts of kaolin.

The indicated active substance is applied to the corresponding carriers (kaolin and chalk) and then these are mixed and ground, to yield wettable powders of excellent wettability and suspension power. By diluting these wettable powders with water it is possible to obtain suspensions of the desired concentration of active substance. Such suspensions are used for controlling weeds and grass-like weeds in crops of cultivated plants by the preemergent method and for treating areas of grass.

Paste: The following substances are used to manufacture a 45% paste:
  45 parts of α-[3-(3',5'-dichloropyridyl-2'-oxy)-6-nitrophenoxy]propionic acid methyl ester
  5 parts of sodium aluminium silicate
  14 parts of cetyl polyglycol ether with 8 moles of the ethylene oxide
  1 part of oleyl polyglycol ether with 5 moles of the ethylene oxide
  2 parts of spindle oil
  10 parts of polyethylene glycol
  23 parts of water.

The active substance is homogeneously mixed with the adjuvants in appropriate devices and ground, yielding a paste from which, by dilution with water, it is possible to obtain suspensions of the desired concentration of active substance. The suspensions are suitable for treating areas of grass.

Emulsifiable Concentrate: The following ingredients are mixed to manufacture a 25% emulsifiable concentrate:
  25 parts of α-[3-(3',5'-dichloropyridyl-2'-oxy)-6-chlorophenoxy]propionic acid isopropyl ester
  5 parts of a mixture of nonylphenolpolyoxyethoxyethylene and calcium dodecylenesulphonate 35 parts of 3,3,5-trimethyl-2-cyclohexan-1-one
35 parts of dimethyl formamide.

This concentrate can be diluted with water to give emulsions in the desired concentrations.

Instead of using the respective active substance indicated in the foregoing formulation examples, it is also possible to use another of the compounds comprised by the formula I.

The active substances of the invention are also of interest for combination with an number of hercides of the phenylurea and triazine series for use in cereal crops, maize, sugar cane, and in fruit culture and viticulture.

The active substances of the formula I are distinguished by a very pronounced preemergent herbicidal action and are thus also strong germination inhibitors.

The following test methods were emloyed to established the usefulness of the compounds of the formula I as herbicides (pre- and postemergent).

Preemergent herbicidal action (germination inhibition)

In a greenhouse, immediately after sowing the test plants in seed dishes the surface of the soil is treated with an aqueous suspension of the active substances obtained from a 25% wettable powder. A concentration was used, which corresponded to 4 kg of active substance per hectare. The seed dishes are then kept in the greenhouse at 22°–25° C. and 50 to 70% relative humidity. The test was evaluated 3 weeks later according to the following rating:

1 = plants have not germinated or are totally withered
2-8 = intermediate stages of damage
9 = plants undamaged (as untreated control).

The results are resumed in the table below:

| Compound number | oats | Sinapis alba | Setaria italica | Stellaria media |
|---|---|---|---|---|
| 2 | 8 | 3 | 2 | 2 |
| 14 | 9 | 2 | 2 | 3 |
| 35 | 9 | 4 | 1 | 2 |
| 53 | 7 | 3 | 2 | 2 |
| 87 | 2 | 1 | 1 | 3 |
| 112 | 2 | 1 | 1 | 1 |
| 114 | 1 | 2 | 1 | 2 |
| 115 | 1 | 1 | 1 | 1 |
| 127 | 2 | 2 | 1 | 2 |
| 144 | 9 | 1 | 1 | 5 |
| 149 | 7 | 2 | 2 | 2 |
| 192 | 9 | 2 | 1 | 1 |
| 201 | 9 | 4 | 1 | 1 |
| 210 | 2 | 1 | 1 | 1 |
| 261 | 2 | 2 | 1 | 7 |
| 297 | 1 | 1 | 1 | 1 |
| 399 | 3 | 1 | 3 | 9 |
| 418 | 9 | 1 | 1 | 1 |

Post-emergent herbicidal action (Contact herbicide)

A number of weeds and cultivated plants, both mono- and dicotyledonous, were sprayed after emergence in the 4- to 6-leaf stage with an aqueous active substance emulsion in a rate of 4 kg of active substance per hectare and kept at 24°–26° C. and 45–60% relative humidity. The test was evaluated, as in the preemergent test, 15 days after treatment in accordance with the same rating. The results are resumed in the table below:

| Compound No. | oats | Setaria italica | Lolium perenne | Sinapis alba | Stellaria media |
|---|---|---|---|---|---|
| 1 | 2 | 1 | 1 | 1 | 1 |
| 2 | 4 | 1 | 2 | 1 | 1 |
| 3 | 4 | 1 | 3 | 2 | 2 |
| 12 | 7 | 1 | 3 | 1 | 2 |
| 16 | 6 | 2 | 3 | 1 | 2 |
| 19 | 5 | 1 | 3 | 1 | 2 |
| 22 | 6 | 2 | 6 | 2 | 1 |
| 27 | 4 | 1 | 2 | 1 | 1 |
| 28 | 6 | 1 | 5 | 3 | 2 |
| 35 | 5 | 1 | 3 | 1 | 1 |
| 41 | 4 | 5 | 4 | 2 | 2 |
| 43 | 4 | 1 | 4 | 1 | 1 |
| 53 | 5 | 2 | 6 | 1 | 2 |
| 55 | 6 | 1 | 3 | 1 | 1 |
| 66 | 4 | 1 | 4 | 2 | 3 |
| 92 | 2 | 1 | 1 | 1 | 3 |
| 95 | 4 | 2 | 3 | 1 | 6 |
| 98 | 4 | 1 | 1 | 1 | 2 |
| 111 | 4 | 2 | 2 | 1 | 2 |
| 113 | 2 | 2 | 2 | 2 | 3 |
| 115 | 2 | 2 | 5 | 1 | 5 |
| 128 | 2 | 1 | 3 | 1 | 1 |
| 129 | 7 | 1 | 6 | 1 | 6 |
| 141 | 4 | 3 | 4 | 1 | 4 |
| 149 | 2 | 1 | 2 | 1 | 1 |
| 192 | 3 | 1 | 1 | 1 | 1 |
| 194 | 3 | 1 | 1 | 1 | 1 |
| 196 | 3 | 1 | 1 | 1 | 1 |
| 200 | 4 | 1 | 2 | 1 | 1 |
| 201 | 7 | 1 | 3 | 1 | 1 |
| 202 | 6 | 2 | 4 | 2 | 2 |
| 204 | 5 | 2 | 3 | 2 | 2 |
| 210 | 1 | 1 | 1 | 1 | 1 |
| 261 | 1 | 1 | 1 | 1 | 1 |
| 297 | 1 | 1 | 1 | 1 | 1 |
| 372 | 4 | 2 | 4 | 2 | 1 |
| 387 | 2 | 1 | 1 | 1 | 1 |
| 399 | 1 | 1 | 2 | 1 | 3 |
| 403 | 2 | 1 | 2 | 1 | 8 |
| 418 | 4 | 1 | 2 | 1 | 4 |
| 426 | 2 | 1 | 3 | 1 | 4 |

We claim:
1. A compound of the formula:

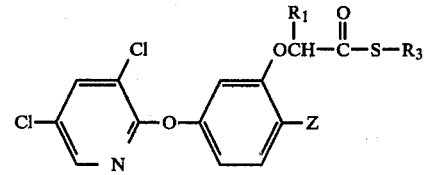

wherein
$R_1$ is methyl, ethyl or methoxymethyl,
$R_3$ is alkyl of 1 to 5 carbon atoms, alkenyl of 3 to 4 carbon atoms, propynyl, phenyl, or —CH$_2$COOCH$_3$, and
Z is chloro, bromo or nitro.

2. A compound according to claim 1 wherein $R_1$ is methoxymethyl.

3. A compound according to claim 1 wherein $R_1$ is ethyl.

4. A compound according to claim 3 wherein Z is nitro and $R_3$ is methyl.

5. A compound according to claim 3 wherein Z is nitro and $R_3$ is ethyl.

6. A compound according to claim 1 wherein $R_1$ is methyl.

7. The compound according to claim 6 wherein Z is chloro and $R_3$ is —CH$_2$COOCH$_3$.

8. The compound according to claim 6 wherein Z is chloro and $R_3$ is —$CH_2C\equiv CH$.

9. The compound according to claim 6 wherein Z is chloro and $R_3$ is —$CH_2C(CH_3)=CH_2$.

10. The compound according to claim 6 wherein Z is chloro and $R_3$ is methyl.

11. The compound according to claim 6 wherein Z is chloro and $R_3$ is isopropyl.

12. The compound according to claim 6 wherein Z is nitro and $R_3$ is —$CH_3COOCH_3$.

13. The compound according to claim 6 wherein Z is nitro and $R_3$ is —$CH_2C\equiv CH$.

14. The compound according to claim 6 wherein Z is nitro and $R_3$ is —$CH_2C(CH_3)=CH_2$.

15. The compound according to claim 6 wherein Z is nitro and $R_3$ is methyl.

16. The compound according to claim 6 wherein Z is nitro and $R_3$ is isopropyl.

17. The compound according to claim 6 wherein Z is bromo and $R_3$ is —$CH_2COOCH_3$.

18. The compound according to claim 6 wherein Z is bromo and $R_3$ is isopropyl.

19. A compound according to claim 6 wherein Z is bromo and $R_4$ is isobutyl or sec. butyl.

20. A herbicidal composition which contains as active ingredient a herbicidally effective amount of a compound according to claim 1 together with an inert carrier.

21. A method for controlling weed at a locus, which comprises applying to said locus a herbicidally effective amount of a compound according to claim 1.

* * * * *